United States Patent [19]

Sarnoff et al.

[11] Patent Number: 4,723,937
[45] Date of Patent: Feb. 9, 1988

[54] PLURAL DOSAGE AUTOMATIC INJECTOR WITH A BY-PASS FITMENT

[75] Inventors: Stanley J. Sarnoff, Bethesda; Claudio Lopez, Silver Spring, both of Md.

[73] Assignee: Survival Technology, Inc., Bethesda, Md.

[21] Appl. No.: 735,740

[22] Filed: May 20, 1985

[51] Int. Cl.⁴ .............................................. A61M 5/00
[52] U.S. Cl. ........................................ 604/90; 604/136
[58] Field of Search ................. 604/136, 236, 82, 89, 604/90, 200, 219, 255, 256, 83

[56] References Cited

U.S. PATENT DOCUMENTS

| | | |
|---|---|---|
| 2,607,341 | 8/1952 | Brown . |
| 2,665,687 | 1/1954 | Brown ................................. 604/89 |
| 3,076,456 | 2/1963 | Hunt ..................................... 604/89 |
| 3,380,449 | 4/1968 | Sarnoff . |
| 3,391,695 | 7/1968 | Sarnoff . |
| 3,424,155 | 1/1969 | Sarnoff . |
| 3,712,301 | 1/1973 | Sarnoff .............................. 604/136 |
| 3,881,484 | 5/1975 | Gidcumb, Jr. ...................... 604/89 |
| 3,882,863 | 5/1975 | Sarnoff et al. . |
| 4,394,863 | 7/1983 | Bartner . |
| 4,439,184 | 3/1984 | Wheeler ............................. 604/90 |
| 4,529,403 | 7/1985 | Kamstra ............................ 604/136 |

FOREIGN PATENT DOCUMENTS 0072057 2/1983 European Pat. Off. .

Primary Examiner—Stephen C. Pellegrino
Attorney, Agent, or Firm—Cushman, Darby & Cushman

[57] ABSTRACT

An automatic injecting device including an elongated housing assembly, a stressed spring assembly mounted within the housing assembly so as to be released in response to a predetermined manual acutation procedure, and a medicament cartridge assembly mounted within the housing assembly in cooperating relation with the stressed spring assembly comprising a hypodermic needle and a medicament container housing forward and rearward individual dosages of different relatively incompatible liquid medicaments mounted therein and separated by a deformable stopper. The medicament container is formed of glass and includes a cylindrical wall open at its rearward end and having an exteriorly flanged necked down forward end portion. A hub assembly connects the exteriorly flanged necked down forward end portion with the hypodermic needle. A separate fitment of molded plastic material is mounted within the interior of the cylindrical glass wall adjacent the necked down forward end portion thereof for radially inwardly deforming the stopper during operation and thereby providing an axial by-pass in the periphery thereof.

9 Claims, 4 Drawing Figures

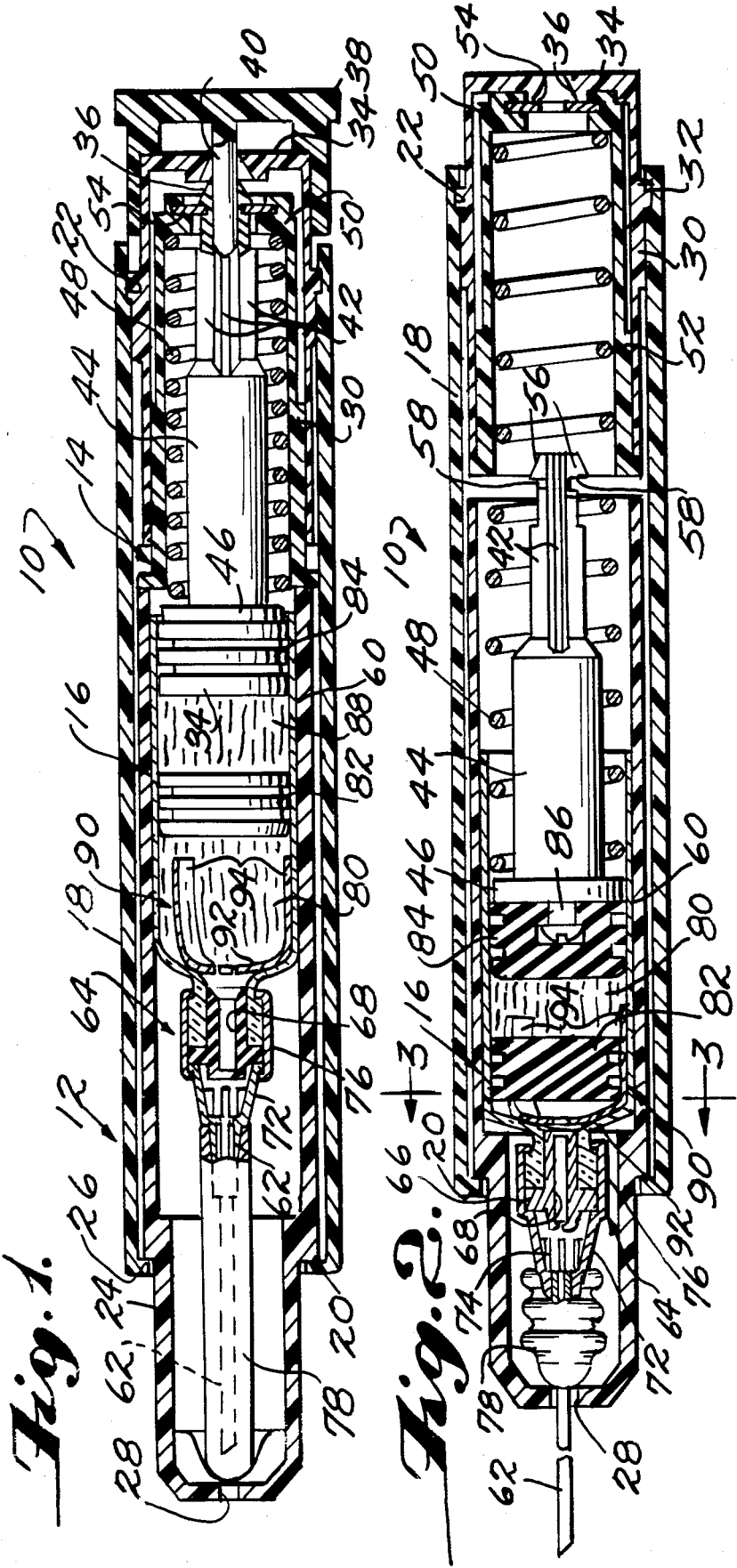
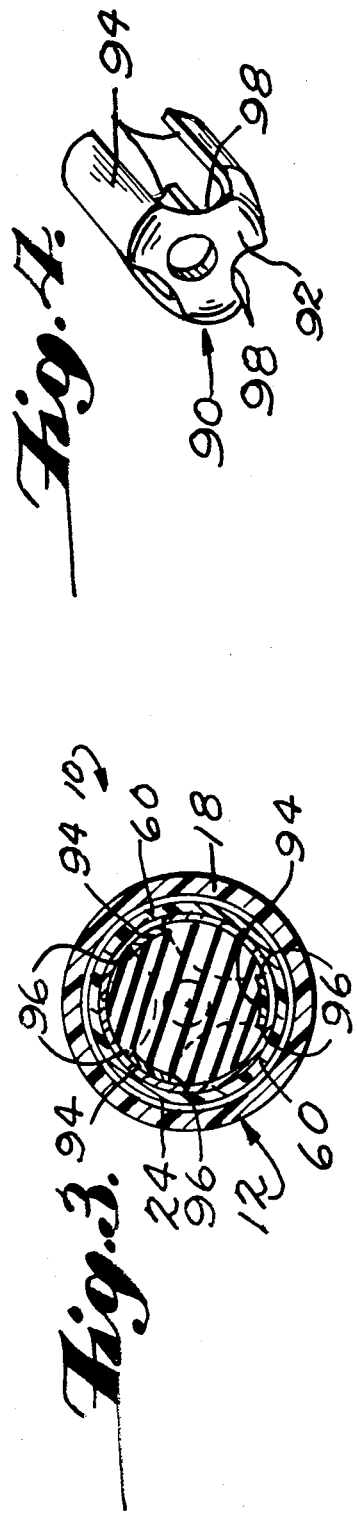

PLURAL DOSAGE AUTOMATIC INJECTOR WITH A BY-PASS FITMENT

This invention relates to plural dosage injectors and more particularly to plural dosage injectors of the automatic type.

The type of injector herein contemplated is disclosed in commonly assigned U.S. Pat. No. 4,394,863, the disclosure of which is hereby incorporated by reference into the present disclosure for background purposes. The injector of the patent includes an elongated housing assembly having a forward end, a stressed spring assembly mounted within the rearward end of the housing assembly so as to be released in response to a predetermined manual actuation procedure and a plural dosage medicament cartridge assembly mounted within the forward end of the housing assembly in cooperating relation with the stressed spring assembly. The cartridge assembly includes the usual medicament container, hypodermic needle and rearward piston. The plural dosages are contained forwardly within the container either by a hub assembly which includes a diaphragm seal or by a resilient sheath which exteriorly surrounds the hypodermic needle. The plural dosages are contained rearwardly by the rearward piston and by one or more intermediate stoppers. In the arrangement shown in the patent, there is a single stopper which provides for two dosages, one a forward dosage forwardly of the stopper and the other a rearward dosage rearwardly of the stopper. In the arrangement disclosed in the patent, a by-pass means is provided for establishing a by-pass around the periphery of the stopper so as to enable the rearward dosage to be forced outwardly through the needle. The specific by-pass arrangement disclosed in the patent consist of forming in the glass container an integral outwardly extending bulge which has an axial extent greater than the axial extent of the stopper. Preferably, the stopper includes a by-pass slot which aids in providing the by-pass for the rearward dosage.

The specification of the patent indicates that other known by-pass arrangements may be employed. One such by-pass arrangement is disclosed in U.S. Pat. No. 2,607,341. In this patent the container is formed of molded plastic and includes two alternative by-pass arrangments, one an integrally molded by-pass groove in the interior periphery of the plastic cylindrical wall of the container, as shown in FIGS. 1 thru 4 and the other, a plurality of integrally molded radially inwardly extending ribs formed integrally on the interior periphery of the plastic cylindrical wall of the container, as shown in FIGS. 5 thru 9.

The inwardly projecting rib configuration disclosed in U.S. Pat. No. 2,607,341 has the advantage that it radially inwardly deforms the stopper to provide peripheral bypass of the stopper, the arrangement being such that the stopper is gripped and held in position. The two embodiments disclosed in U.S. Pat. No. 2,607,341 quite clearly suggest that the outwardly extending integral bump or by-pass provided in U.S. Pat. No. 4,394,863 could just as easily be provided as an integral inwardly extending bump and such an arrangement is disclosed in FIG. 4 of published European patent application No. 0,072,057. This published patent application also illustrates that it is within the contemplation of the prior art to form the container into two separate parts, one a simple cylindrical tube and the other a forwardly extending portion having a neckdown end. In the arrangement shown in FIG. 1 of the published European patent application, the tubular part is made of glass and the forward neckdown part is molded of plastic material.

It will be understood that the forming of the container entirely or partially of plastic material presents a different containment problem than is presented by the use of a one piece glass container. However, with the necessity to provide an integral by-pass bulge in the glass container wall the advantages of utilizing glass and the cost involved likewise become problematical. What is needed is an arrangement which is capable of utilizing the conventional glass construction in the container while providing the by-pass in a much simpler and more economical manner than integral formation.

It is an object of the present invention to fulfill that need. In accordance with the principles of the present invention, this objective is obtained by providing an automatic injecting device including an elongated housing assembly, a stressed spring assembly mounted within the housing assembly so as to be released in response to a predetermined manual actuation procedure, and a medicament cartridge assembly mounted within the housing assembly in cooperating relation with the stressed spring assembly. The medicament cartridge assembly comprises a hypodermic needle and a medicament container housing forward and rearward individual dosages of different relatively incompatible liquid medicaments mounted therein and separated by a deformable stopper. The medicament container is formed of glass and includes a cylindrical wall open at its rearward end and having an exteriorly flanged necked down forward end portion. A hub assembly connects the exteriorly flanged necked down forward end portion with the hypodermic needle. A separate fitment of molded plastic material is mounted within the interior of the cylindrical glass wall adjacent the necked down forward end portion thereof for radially inwardly deforming the stopper during operation and thereby providing an axial by-pass in the periphery thereof.

While the invention is particularly suitable for use in automatic injectors, the structure and functional principles of the invention can also be readily embodied in a manually actuated prefilled syringe assembly.

Another object of the present invention is the provision of a plural medicament container assembly having separate sequentially injectable medicaments and an improved by-pass arrangement which is simple in construction, effective in operation and economical to manufacture and maintain.

These and other objects of the present invention will become more apparent during the course of the following detailed description and appended claims.

The invention may best be understood with reference to the accompanying drawings, wherein an illustrative embodiment is shown.

In the drawings:

FIG. 1 is a longitudinal sectional view of an automatic injector embodying the principles of the present invention showing the same in its normal storage position;

FIG. 2 is a view similar to FIG. 1 showing the posiiton of the parts just prior to the completion of the injection operation;

FIG. 3 is a sectional view taken along the line 3—3 of FIG. 1; and

FIG. 4 is a perspective view of the separate by-pass fitment constructed in accordance with the principles of the present invention.

Referring now more particularly to the drawings, there is shown therein an automatic injector, generally indicated at 10, which embodies the improvements of the present invention. The injector consists essentially of three basic assemblies: one, a housing assembly, generally indicated at 12; two, a power pack or stressed spring assembly, generally indicated at 14, mounted within the rearward end portion of the housing assembly 12 and operable in response to a predetermined manual actuating procedure to be released so as to operate the third assembly, which is a plural medicament cartridge assembly, generally indicated at 16, embodying the improvements of the present invention. While the housing assembly 12 and stressed spring assembly 14 can assume any known configuration, the preferred embodiment as shown is constructed in accordance with the teachings contained in U.S. Pat. Nos. 3,712,301 and 3,882,863, which disclosures are hereby incorporated by reference into the present specification.

As best shown in FIGS. 1 and 2, the housing assembly 12 includes an outer tubular member 18 having a radially inwardly turned flange 20 on the forward end thereof and an interior annular groove 22 in the rearward end thereof. The housng assembly 12 also includes an inner tubular member 24 having a forward end portion of reduced diameter defining an exterior forwardly facing shoulder 26 which is adapted to engage the forward flange 20 of the outer tubular member 18 when the inner tubular member is disposed therein in operative position. The inner tubular member 24 includes a forward end having a needle opening 28 therein and the interior of the inner tubular member is configured to receive the cartridge assembly 16.

The stressed spring assembly 14 as preassembled includes an outer tubular member 30 having an annular ridge 32 formed on the exterior periphery thereof adjacent the rearward end portion which serves to engage within the annular groove 22 of the outer tubular member 18 when the injector is assembled in operative position, as shown in FIG. 1. The outer tubular member 30 includes a rearward end wall 34 having a central opening therein defined by a frustoconical surface 36 which diverges inwardly. The stressed spring assembly includes a safety cap 38 which detachably fits over the portion of the outer member 30 extending rearwardly from the outer tubular member 18. The safety cap 38 includes a central inwardly extending safety pin 40 which in its normal preassembly position extends through and inwardly of the frustoconical surface 36.

The safety pin 40 is adapted to cooperate with a plurality of spring fingers 42 extending from the rear end of a plunger 44 having an annular flange 46 extending rearwardly outwardly from the forward end thereof. The rearward surface of the flange 46 is adapted to engage one end of a stressed coil spring 48, the other end which engages an apertured rear wall 50 of a tubular member 52 slidably mounted within the tubular member 30. The apertured end wall 50 has formed therein an apertured catch plate or disc 54. The central opening of the catch plate 54 is of a size to engage inclined surfaces 56 formed on the outer rearward portions of the spring fingers 42 so as to deflect the fingers radially inwardly as the rearward ends of the fingers pass rearwardly therethrough. Each spring finger 42 has formed therein an exterior catch receiving notch 58 which is adapted to receive the catch plate 54 when the spring fingers have been moved rearwardly through the catch plate into the normal spring stressed preassembly position, as shown in FIG. 1. In this regard it will be noted that safety pin 40 engages within the inner surfaces of the spring fingers 42 and hence prevents their radially inward movement so that the tubular members 30 and 52, plunger 44 and safety cap 38 can be preassembled and mounted in operative position within the outer tubular member 18 as a unit. In the operative positon, the members 30 and 52 of the power pack assembly 14 may be regarded as part of the housing assembly 12. Preferably, members 30 and 52, as well as members 18 and 24, are made of a suitable plastic material, as is indicated in the aforesaid patents.

The cartridge assembly 16 which is constructed in accordance with the principles of the present invention includes a medicament container 60 which, as shown, is preferably made of glass and is essentially in the form of a necked bottomless bottle having a substantially cylindrical peripheral wall. The cartridge assembly also includes a hypodermic needle 62 which is disposed forwardly of the container 60 and has its rearward end connected with the necked end of the container 60 by a connecting assembly, generally indicated at 64. The connecting assembly 64 is preferably constructed in accordance with the teachings contained in commonly assigned U.S. Pat. No. 3,380,449 (see also U.S. Pat. Nos. 3,391,695 and 3,424,155), the disclosures of all of which are hereby incorporated by reference into the present specification. As shown, the assembly 64 includes a resilient stopper 66 engaged within the necked end of the container 60, the stopper providing central passage 68 which leads to an exterior integral resilient diaphragm seal 70. Disposed in exterior engagement with the stopper 66 is a fitting 72. A rearward sleeve portion 74 of the fitting 72 is engaged over the forward marginal and outer periphery of the stopper 76 and the neck portion of the container 60 and has its rearward end turned down to effectively secure the components of the assembly in operative position. A reduced forward end portion 76 of the fitting 72 fixedly receives a portion of the hypodermic needle 62 spaced slightly from the rearward end thereof. As shown, the rearward end of the hypodermic needle is sharpened, as indicated at 77, and positioned in forwardly spaced relation from the seal 70.

In accordance with the principles set forth in U.S. Pat. No. 3,882,863, the remaining forwardly extending portion of the hypodermic needle 62 is encased within a rubber sheath 78 which serves the dual funciton of maintaining the needle in a sterile condition when the injector 10 is in its storage condition and to provide a shock absorbing effect during the injection procedure, all in accordance with the teachings set forth in the aforesaid patent. Where the nature of the medicament within the container is compatable with the metal of the needle, diaphragm seal 70 may be omitted and the sheath 78 may be utilized for a third function, namely, that of normally containing the forward medicament from flowing out of the end of the needle during storage.

The cartridge assembly 16 includes a first liquid medicament 80 within the container 60 between the forward seal provided by the diaphragm 70 (or the sheath 78) and an intermediate resilient stopper 82.

Mounted within the rear open end of the container 60 is a rearward piston 84. This piston is similar in construction to the stopper 82 except that it has a hollow interior configured to receive a central projection 86 extending forwardly from the plunger 44 so as to provide an interconnection between the same. The cartridge assembly 16 includes a second relatively incompatible liquid medicament 88 disposed within the container 60 between the interior seal provided by the intermediate stopper 82 and the rear seal provided by the rearward piston 84.

In accordance with the principles of the present invention, a separate by-pass fitment, generally indicated at 90, which is molded of a suitable plstic material, as for example, polyethylene, is mounted within the forward end portion of the container 60. By-pass fitment 90 is operable to be engaged by the stopper 82 as the latter moves forwardly during the operation so as to deform the stopper 82 radially inwardly as its forward movement is arrested so as to provide by-pass means around the exterior periphery of the stopper for the flow of the second liquid medicament 88 as the forward movement of the piston 84 continues.

As best shown in FIGS. 3 and 4, the by-pass fitment 90 includes a molded plastic body having a centrally apertured forward annular portion 92 and a plurality of annularly spaced portions 94 extending longitudinally rearwardly therefrom in engagement with the interior surface of the cylindrical wall of container 60. It will be noted that the longitudinal extent of the portion 94 is greater than the axial extent of stopper 82. Viewed in terms of the position of the rearward surface of the stopper 82, the longitudinal extent is less than the distance between the forward necked down end of the container 60 and the rearward surface of the stopper 82 when the latter is in its storage position but greater than this distance after the stopper 82 has been moved into its forwardmost position.

It is within the contemplation of the present invention to provide more than two liquid medicaments in the container 60. For example, when three medicaments are provided there would be provided two stoppers, for four medicaments, three stoppers and so forth. The longitudinal extent of the fitment portions 94 must still be less than the distance between the forward necked down end of the container 60 and the rearward surface of the forwardmost stopper when in its storage position and greater than the distance between the forward necked down end of the container 60 and the rearward surface of the rearwardmost stopper when the latter has reached its forwardmost position.

It will be understood that any two liquid medicaments may be utilized in the apparatus 10 as shown. One example, as a nerve gas antidote, is atropine and pralidoxine chloride with a water diluent and Valium with a prophylene glycol diluent. Another example, as a coronary reperfusion treatment, is t-PA and hydroxylamine hydrochloride. It will also be understood that the fitment 90 will work with equal facility in conjunction with a stopper forming a part of a plural dosage prefilled syringe.

When it is desired to inject the medicaments, the safety cap 38 is initially removed, thus displacing the safety pin 40 from its storage position within the spring fingers and hence permitting the same to move radially inwardly.

The actuation procedure consists in the operator manually gripping the exterior periphery of the outer tubular member 18 and then moving the injector forwardly into contact with the muscle tissue to be injected, as for example, the patient's thigh. When the forward end of the inner member 18 engages the exterior of the thigh, continued forward movement exerted on the exterior periphery of the outer member results in relative longitudianl movement between rear end walls 50 and 34, causing the frustoconical surface 36 to engage the spring finger surfaces 56 and thus move the same radially inwardly by a camming action so as to disengage the grooves 58 from the catch plate, thus releasing the stressed spring 48. As the stressed spring 48 is released the entire cartridge assembly 16 is moved forwardly within the housing assembly 12 during which time the forward pointed end of the hypodermic needle 62 moves outwardly through the sheath 78 and opening 28 and into the muscle tissue of the patient. Rubber sheath 78 is compressed during this movement and this compression serves to retard the final forward movement of the cartridge with a shock absorbing effect. As the forward movement of the container 60 and needle 62 is retarded, the released stressed spring 48 continues to move the plunger 44 forward which carries with it the rearward piston 84. The adjacent rearward liquid medicament 88 within the container 60 is placed under pressure in response to the initial movement of the rear piston 84. The pressurized liquid medicament 88 transmits the movement of the rearward piston 84 to the intermediate stopper 82, thus pressurizing the forward liquid medicament 80, causing the diaphragm seal 70 sealing the forward end of the liquid medicament 80 to bulge forwardly. In the event that this bulging movement does not serve to burst the diaphragm 70 prior to the engagement with the sharpened rear end 77 of the hypodermic needle 62, the engagement with the sharpened rear end 77 insures that the diaphragm 70 will burst, allowing the pressurized liquid medicament 80 in pressure communication therewith to pass into the forward portion 76 of the fitting 72 and forwardly through the hypodermic needle 62 outwardly into the muscle tissue of the patient.

Movement of the forward liquid medicament 80 outwardly through the hypodermic needle 62 will continue until the forward movement of the stopper 82 engages the fitment 90 and moves into close proximity to the annular portion 92 thereof. It will be noted, however, that the axial extent of the portion 94 is greater than the axial thickness of the stopper 82 so that when the stopper 82 reaches a position spaced slightly rearwardly of the forward necked end of the container 60, the fitment 90 provides by-pass means for the flow of the rearward liquid medicament 88 forwardly from a position rearwardly of the rear surface of the stopper 82 to a position forwardly of the forward surface thereof. The longitudinal portions 94 of the fitment engage and deform radially inwardly annularly spaced portions of the periphery of the stopper 82. The by-pass means is defined at each deformation by the slight longitudinal passages 96 along opposite sides of each portion 94. It will be noted that the periphery of the annular portion 92 of the fitment 90 between the portions is cut back, as indicated at 98, to insure communication of the forward ends of the by-pass passages 96 with the interior of the needle 62.

FIG. 2 illustrates the position of the parts just after forward movement of the stopper 82 has been halted. During the remainder of the forward movement of the rearward piston, the rearward liquid medicament 88 is forced outwardly through the by-pass passages 96 by the fitment 90 and outwardly through the hypodermic needle 62 into the muscle tissue of the patient. It will be noted that when the forward surface of the rearward piston 84 engages the rearward surface of the stopper 82, the rearward peripheral portion of the piston 84 has not yet reached the ends of the fitment portions 94.

It will be understood that the above described operation of the automatic injector 10 takes place quite rapidly so that in so far as the patient is concerned the operation occurs so rapidly after the actuating procedure has been performed as to require the operator simply to withdraw the needle after a few seconds have elapsed. It can thus be seen that by the improvements embodied in the cartridge assembly of the present invention it becomes possible to effectively independently store a plurality of relatively incompatible liquid medicaments within an automatic injector and to effectively sequentially inject the liquid medicaments in a conventional automatic fashion by an arrangement which is economical in its simplicity when compared with similar arrangements.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In an automatic injecting device including an elongated housing assembly having a forward end, stressed spring means mounted within said housing assembly so as to be released in response to a predetermined manual actuation procedure, and a medicament injection cartridge assembly mounted within said housing assembly in cooperating relation with said stressed spring means, said medicament injection cartridge assembly comprising a medicament container, a hypodermic needle disposed forwardly of said container mounted within said housing assembly adjacent the forward end thereof, a rearward piston mounted in the rearward end of said container for forward movement therein in slidably sealed relation thereto, forward and rearward individual liquid medicaments within said container with said rearward liquid medicament in rearwardly sealingly contained relation with respect to said piston, movable intermediate sealing means within the interior of said container forwardly of said piston for containing the individual liquid medicaments sealingly separated from one another, containment means associated with said needle operable prior to the release of the stressed spring means to provide (1) containment of a sterile environment for the exterior of said needle and (2) containment of the forward liquid medicament against passage forwardly beyond said sterile environment, said containment means including a resilient sheath within the housing assembly exteriorly covering said needle, means operable in response to the manual accomplishment of said manual actuating procedure and the resultant release of said stressed spring means for moving said piston forwardly and hence initially the entire cartridge assembly therewith including the hypodermic needle forwardly and outwardly of said sheath and said housing assembly into the muscle tissue of a patient, means operable in response to the arresting of the forward movement of the container of said assembly by the compression of said resilient sheath when said needle has been moved into the muscle tissue of a patient and the continued forward movement of said piston within said container for causing said forward liquid medicament to move outwardly of said needle by virtue of the forward movement of said intermediate sealing means with respect to said container, and by-pass means operable in resonse to the forward movement of said intermediate sealing means toward and into a forward limiting position within said container and the continued forward movement of said piston within said container for causing the rearward liquid medicament to move out of sealed relation with said intermediate sealing means and into communication with said needle for movement outwardly thereof in response to the continued forward movement of the piston, the improvement which comprises said medicament container being formed of glass, said glass container including a cylindrical wall open at its rearward end and having an exteriorly flanged necked down forward end portion, a hub assembly connecting the exteriorly flanged necked down forward end portion with said hypodermic needle, said by-pass means comprising separate fitment means of molded plastic material mounted within the interior of said cylindrical glass body adjacent the necked down forward end portion thereof for radially inwardly deforming said movable intermediate sealing means and thereby providing axial by-pass means in the periphery thereof, said fitment means including a molded plastic body engaged as a fitment with said cylindrical wall.

2. The improvement as defined in claim 1 wherein said molded plastic body includes a centrally apertured forward annular portion of an exterior diameter sufficient to extend to said cylindrical wall and a plurality of annularly spaced portions extending longitudinally rearwardly therefrom in engagement with said cylindrical wall.

3. The improvement as defined in claim 2 wherein said movable intermediate sealing means includes a resilient stopper disposed a first predetermined distance from the necked down forward end portion of said container in confining relation to the forward portion of the rearward liquid medicament when said cartridge assembly is in cooperating relation with said stressed spring means before the release thereof and being spaced a shorter second predetermined distance from the necked down forward end portion of said container after said piston has been moved into its forward most position following the release of said stressed spring means, said stopper having a radially inwardly deformable periphery slidably sealingly engaged with the interior periphery of said cylindrical wall, said annularly spaced fitment portions extending rearwardly from the necked down forward end portion a distance less than the first predetermined stopper spacing distance and greater than the second predetermined stopper spacing distance.

4. The improvement as defined in claim 3 wherein said containment means further includes a burstable diaphragm within said hub assembly between said needle and said forward liquid medicament for containing the latter forwardly out of contact with said needle.

5. The improvement as defined in claim 1 wherein said containment means further includes a burstable diaphragm within said hub assembly between said needle and said forward liquid medicament for containing the latter forwardly out of contact with said needle.

6. The improvement as defined in claim 2 wherein said containment means further includes a burstable diaphragm within said hub assembly between said needle and said forward liquid medicament for containing the latter forwardly out of contact with said needle.

7. An injecting device including a prefilled plural medicament container assembly comprising
   a glass container including a cylindrical wall open at its rearward end and having a necked down forward end portion adapted to have a hypodermic needle connected therewith,
   a piston slidably sealingly mounted within the open rearward end of said cylindrical wall,
   radially inwardly deformable stopper means slidably sealingly mounted within said cylindrical wall between said piston and the necked down forward end thereof dividing the interior of said cylindrical wall between said piston and the necked down forward end thereof into a plurality of spaces,
   a plurality of separate liquid medicaments in said plurality of spaces,
   and separate fitment means of molded plastic material mounted within the interior of said cylindrical wall adjacent the necked down forward end portion thereof operable in response to the movement of said piston forwardly through an injecting stroke within said cylindrical wall for (1) engaging said stopper means during liquid medicament transmitted movement thereof with said piston and (2) deforming said stopper means radially inwardly so as to provide axial by-pass means in the periphery thereof.

8. An injecting device as defined in claim 7 wherein said molded plastic body includes a centrally apertured forward annular portion of an exterior diameter sufficient to extend to said cylindrical wall and a plurality of annularly spaced portions extending longitudinally rearwardly therefrom in engagement with said cylindrical wall, said fitment means including a molded plastic body engaged as a fitment with said cylindrical wall.

9. An injecting device as defined in claim 8 wherein said stopper means includes a resilient stopper disposed a first predetermined distance from the necked down forward end portion of said container in confining relation to the forward portion of the rearward liquid medicament when said cartridge assembly is in cooperating relation with said stressed spring means before the release thereof and being spaced a shorter second predetermined distance from the necked down forward end portion of said container after said piston has been moved into its forward most position following the release of said stressed spring means, said stopper having a radially inwardly deformable periphery slidably sealingly engaged with the interior periphery of said cylindrical wall, said annularly spaced fitment portions extending rearwardly from the necked down forward end portion a distance less than the first predetermined stopper spacing distance and greater than the second predetermined stopper spacing distance.

* * * * *